United States Patent [19]
Andrä et al.

[11] Patent Number: 6,082,366
[45] Date of Patent: Jul. 4, 2000

[54] METHOD AND ARRANGEMENT FOR DETERMINING THE POSITION OF A MARKER IN AN ORGANIC CAVITY

[75] Inventors: Wilfried Andrä; Klaus Eitner, both of Jena; Rudolf Hergt, Apolda, all of Germany

[73] Assignees: Aesculap Meditec GmbH; Institut fuer Physikalische Hochtechnologie e.V., both of Jena, Germany

[21] Appl. No.: 09/011,465

[22] PCT Filed: Sep. 3, 1996

[86] PCT No.: PCT/EP96/03857

§ 371 Date: Feb. 9, 1998

§ 102(e) Date: Feb. 9, 1998

[87] PCT Pub. No.: WO97/09640

PCT Pub. Date: Mar. 13, 1997

[30] Foreign Application Priority Data

Sep. 5, 1995 [DE] Germany .......................... 195 32 676

[51] Int. Cl.[7] .................................................. A61B 19/00
[52] U.S. Cl. ............................................................ 128/899
[58] Field of Search ...................................... 128/897–99

[56] References Cited

FOREIGN PATENT DOCUMENTS

| 39 40 260 | 9/1990 | Germany . |
| 60-128385 | 7/1985 | Japan . |
| 60-129681 | 7/1985 | Japan . |

OTHER PUBLICATIONS

M. Reiser, W. Semmler (Hrsg) "Magnetresonanztomgraphie", Springer–Verlag, Berlin/Heidelberg, 1992.

M. Amend, C. Jakobeit, L. Greiner, Verdauungskrankheiten 13 (1995), vol. 1, p. 21.

K. Ewe, Therapiewoche 41 (1991), p. 77.

Y. Benmair, B. Fischel, E.H. Frei, T. Gilat, The American Journal of Gastroenterology 68 (1977), p. 170.

L. Trahms, R. Stehr, J. Wedemeyer, W. Weitschies, Biomedizinische Technik 35 (1990), p. 158.

K. Fitzgerald, IEEE Spectrum 27 (1990), p. 52.

W. Weitschies, J. Wedemeyer, R. Stehr, L. Trahms, IEEE Trans. Biomed. Eng. 41 (1994), p. 192.

*Primary Examiner*—John P. Lacyk
*Attorney, Agent, or Firm*—Jordan and Hamburg LLP

[57] ABSTRACT

The invention concerns a method and an arrangement for determining the position of a marker in an organic cavity, in particular for establishing local passage speeds within the framework of the medical diagnosis of the stomach-bowel tract. The object of the invention is to provide a solution which ensures position-determining accuracy of greater than 1 cm in all three co-ordinate directions and permits position-determining times of 10 seconds and less in each case. According to the invention, this object is achieved in that at least one coil is acted upon in a time interval in a pulsed manner by current whose sign changes in each case between two current pulses, when the primary magnetic field, of the coil, produced thereby has died out to sufficiently low values. The secondary magnetic field generated by a marker is measured separately at least once by anisotropic magnetic field sensors parallel and perpendicular to the coil axis. The coil arrangement is displaced relative to the marker until the magnetic field sensors used to determine the radial component of the secondary magnetic field of the marker supply a zero signal and the associated position of the coil axis and the associated measured values supplied by the magnetic field sensors used to detect the secondary magnetic field component of the marker, which component runs parallel to the coil axis, are stored and fed to a display.

15 Claims, 4 Drawing Sheets

METHOD AND ARRANGEMENT FOR DETERMINING THE POSITION OF A MARKER IN AN ORGANIC CAVITY

BACKGROUND OF THE INVENTION

The invention relates to an arrangement for and method of determining the position of a marker in an organic cavity, in particular for determining local passage speeds of a marker while passing the gastro-intestinal tract, particularly the small bowel area. The invention is applicable within the frame of medical diagnosis of the gastro-intestinal tract and does not concern a diagnosis procedure per se.

There are medical examinations known which require a repeated detection of the local passage speeds of a marker while passing the gastro-intestinal tract. This is the case, for example, with chronic inflammatory intestinal diseases such as Morbus Chron, functional gastro-intestinal diseases, and in physiological examinations of the gastro-intestinal tract. The conventional diagnosis techniques such as X-ray examination under use of contrast meals are not applicable in such cases due to the radiation exposure. The same comes true for scintigraphic methods.

A radiation exposure is avoided with known techniques such as the nuclear spin tomography [M. Reiser, W. Semmler (editor) "Magnetoresonanztomographie", Springer press, Berlin/Heidelberg, 1992] the sonography [M. Amend, C. Jakobeit, L. Greiner, Verdauungskrankheiten 13 (1995), No. 1, pg. 21], the use of metal detectors [K. Ewe, Therapiewoche 41 (1991), pg. 77], the inductive detection of soft magnetic tracers [Y. Benmair, B. Fischel, E. H. Frei, T. Gilat, The American Journal of Gastroenterology 68 (1977), pg. 170], and the local position detection of permanent magnetic markers [L. Trahms, R. Stehr, J. Wedemeyer, W. Weitschies, Biomedizinische Technik 35 (1990), pg. 158].

The nuclear spin tomography or the magneto-resonance is an expensive method which is not suitable for examinations which have to be repeated very often, apart from being too slow for the detection of local passage speeds, which require time intervals in an order of size of 10 s. for the successive position detection of markers [K. Fitzgerald, IEEE Spectrum 27 (1990), pg. 52].

Sonographic examinations have not been employed for the detection of local passage speeds up to now, but only for measuring general transit times of larger sections of the gastrointestinal tract [M. Amend, C. Jakobeit, L. Greiner, Verdauungskrankheiten 13 (1995), No. 1, pg. 21], since air volumes in the abdominal cavity cannot be penetrated by ultrasound and will result in a faulty position detection of the marker. Such deficiencies could be reduced by completely filling the bowel with a liquid, however, a filled bowel is not suited for a diagnosis due to the changed peristalsis.

It is feasible to determine the position of metal particles by metal detectors. However, the lateral accuracy of the position detection decreases with the increasing distance from the body surface and is worse than 1 cm at a distance of >10 cm [K. Ewe, Therapiewoche 41 (1991), pg. 77]. Said paper does not report of the accuracy of depth-measurements. Since the accuracy of depth-measurements is generally worse than the lateral accuracy this method is insufficient for local passage speed measurements.

The accuracy of position detection obtained with an inductive measurement of a soft-magnetic tracer satisfies examinations of the gastric contents decrease per unit time of a soft-magnetic meal having an initial volume of more than 100 cm3 [Y. Benmair, B. Fischel, E. H. Frei, T. Gilat, The American Journal of Gastroenterology 68 (1977), pg. 170]. However, on the one hand, a measurement of the local passage-speed in the bowels is not feasible, since the large test meal volume uncontrollably distributes while passing the bowels. On the other hand, the test volume cannot be reduced substantially since otherwise the secondary magnetic field produced by the tracer, even when highly compensated, will become so small that it cannot be separated from the residual signal of a primary magnetic field applied during measurement.

Furthermore, it is known to magnetically charge-up permanent magnetic markers before being administered to a patient [W. Weitschies, J. Wedemeyer, R. Stehr, L.Trahms, IEEE Trans. Biomed. Eng. 41 (1994), pg. 192]. However, the detection of the position of the markers via their secondary magnetic field is considerably affected by interference fields (for example, by the magnetic field of the earth) so that the measurements have to be carried out in an extremely magnetically screened special chamber. Even then this method is not suitable for a detection of the local passage speed in the entire gastro-intestinal tract. Hence, a position detection is only feasible in the stomach and in the large bowel, due to the transversal and rotational movements of the marker, and even in these ranges, where the retention time of the marker is comparatively high, the accuracy is insufficient.

SUMMARY OF THE INVENTION

It is an object of the present invention to provide an arrangement for and method of determining the position of a marker in an organic cavity, in particular in the gastro-intestinal tract, which ensures an accuracy of the position determining of better than 1 cm along the three coordinate directions, and times for each position detection of equal to or less than 10 s. Furthermore, it is feasible to exploit the measuring values of a respective marker position obtained by solution for a three-dimensional representation.

According to the invention a magnetizable marker is employed which consists of a spherosymmetrically distributed isotropic semi-hard magnetic material of medium coercive force, preferably within a range of from $10^4$ up to $10^5$ A/m, and a high relative residual magnetism of preferably >0.8. It is feasible to provide said marker singly, or in a viscous excipient solution, or in connection with a solid excipient (capsule). Preferably the marker is substantially made of $\gamma\text{-Fe}_2\text{O}_3$ and/or $\text{Fe}_3\text{O}_4$ which, apart from having the required magnetic properties, is non-toxic. The marker is inserted into an organic cavity and exposed to a primary magnetic field applied by an electric coil which, in turn, is subject to a pulse-shaped current. The coil diameter has to be dimensioned to at least fivefold the marker diameter. It is essential that the coil be embodied in such a manner that it produces an axially symmetrical and substantially homogeneous primary magnetic field over a range having the dimensions of about 10·10·30 cm³. While the marker passes the organic cavity, the magnetism of the marker is charged-up repeatedly and at short time intervals by the coil excited by the pulse-shaped current. Thus the magnetic moment of the marker is readjusted to be in parallel to the primary magnetic field of the coil. In this manner, the rotational movement of the marker which, otherwise, may falsify the measuring value, becomes insignificant. By means of anisotropic magnetic field sensors, at least one measurement of the secondary magnetic field of the marker is carried out between two respective pulses, when the primary magnetic field of the coil has decreased to values preferably less than 10% of the maximum value. The time intervals of the maxima of the primary magnetic field can be adapted to the gastro-intestinal tract ranges and are dimensioned to be short enough to eliminate otherwise interfering translatory or rotational movements of the marker or to compensate the same by mean value formation out of a plurality of measurements. The time interval preferably is set to <10 s.

Advantageously, the primary magnetic field according to the invention is generated by a couple of coaxially arranged coils between which the body range of the patient to be under examination is placed. The distance of the coil has to be adapted to the body of the patient, and preferably ranges between 30 cm and 40 cm. The direction of the primary magnetic field is in parallel to the common axis of the two coils and the polarity is preferably reversed in two subsequent magnetical chargings. The maximum value Hp of the primary magnetic field is selected to produce a sufficiently high residual magnetism in the marker. It is advantageous, depending on the marker material selected, to produce an $H_p$ of $>10^3$ A/m. Towards higher values $H_p$ is only limited by the technical expenditures, it can amount up to $10^5$ A/m with, for example, pulsed fields.

The secondary magnetic field $H_s$, produced by the residual magnetism of the marker can be described—at a distance from the marker center which is at least three-times the marker diameter—with sufficient accuracy as a dipole field by the equations $$H_s = \frac{m}{R^3}\sqrt{(1+3\cos^2\vartheta)} \quad (1)$$

$$\tan \Phi = 0.5 \tan \vartheta \quad (2)$$

wherein m is the magnetic moment of the marker, R is the distance between the marker center and the place of the secondary magnetic field, and $\Phi$ and $\upsilon$ are the angles defined in FIG. 2. The components of the secondary magnetic field parallel $H_s^\parallel$ and perpendicular $H_s^\perp$ to the direction of residual magnetism are described by the equations $$H_s^\parallel = H_s \cos (\upsilon + \Phi) \quad (3)$$

$$H_s^\perp = H_s \sin (\upsilon + \Phi) \quad (4)$$

It is feasible to separately measure the components by means of suitable magnetic field sensors, preferably anisotropic magnetoresistive thin layer sensors, as presently on sale. $\upsilon = \Phi = 0$ is valid for the axis of the secondary magnetic field defined by the m-direction. Hence, with given values for m and R, the amount of $H_s^\parallel$ is a maximum, while $H_s^{195}$ is zero at the same time. As soon as the marker is on the coil axis, a magnetic field sensor arranged on the respective coil axis only indicates a possibly existing interfering field for $H_s^{195}$. However, when the marker deviates from the coil axis, the magnetic field sensor produces an additional signal, the sign of which changes with the polarity of the primary magnetic field. This frequency-selective and amplified signal from the respective magnetic field sensor indicates whether or not the marker is on the coil axis. With small angles $\upsilon$ and $\Phi$, $H_s^\perp$ is a monotonic function of the distance r between the marker center and the coil axis (and said at least one magnetic field sensor secured to said axis) and becomes zero with r=0. Hence, a zero-balancing of the signal is feasible by displacing the field axis (with the magnetic field sensor secured thereto) relative to the marker. Thus, according to the invention, the coil axis is aligned with to the marker center. It is feasible to symmetrically secure a second magnetic field sensor to the coil axis for detecting $H_s^\perp$. The signal from the second sensor is added with reversed sign to the signal from the first one. Furthermore, it is feasible to radially arrange a plurality of such magnetic field sensors on and to distribute them in axial symmetry about said coil axis, and to electrically interconnect them in analogy to the above mentioned.

According to equation (1), the amount of $H_s$ is a unique function of R at a given value m of the magnetic moment, as soon as the marker is on the coil axis ($\upsilon = \Phi = 0$). When, in a special case, two equal coils are employed, arranged coaxially to one another, and the marker is centrally positioned between said two coils, wherein one $H_s^\parallel$-magnetic field sensor is provided for each coil, equally spaced to the respective coil and to the common coil axis, then $H_s$ is equal at the place of the two magnetic field sensors. When both sensors are of equal sensitivity the difference between the signals is zero. When the marker position on the coil axis deviates from the central position by a space z, the difference signal is a monotonic function of z and, with m known, a measure for the deviation of the marker in z-direction is made. It is feasible to determine the value of m in a separate measuring step before and/or after the marker is and has been administered, respectively, to the patient. The accuracy of measurement in z-direction can be improved, in analogy to the detection in radial direction, in that further $H_s^\parallel$-magnetic field sensors are arranged about the coil axis which are respectively connected. Hence, the actual position of the marker within the organic cavity is entirely determined, on the one hand, by the position of the coil axis, which is recorded by suitable means, after zero-balance of the $H_s^\perp$-signal by suitable displacement means and, on the other hand, by the size of the $H_s^\parallel$-signal.

Reference markers in the shape of small coils and magnets, respectively, are attached to the patient's body at definite places, the positions of which also are measured, in order to determine the marker position relative to the patient's body for an initial and intermediate, respectively, positioning of the patient. The determination of the local passage speed of the marker simply results as a quotient from the respective distance of two measuring points between two respective current pulses applied across the coil(s) and the time difference of said adjacent measuring points.

BRIEF DESCRIPTION OF THE DRAWINGS

In order that the invention may be more readily understood reference is made to the accompanying four drawings which illustrate diagrammatically and by way of example one embodiment thereof.

DETAILED DESCRIPTION

Figure 1:
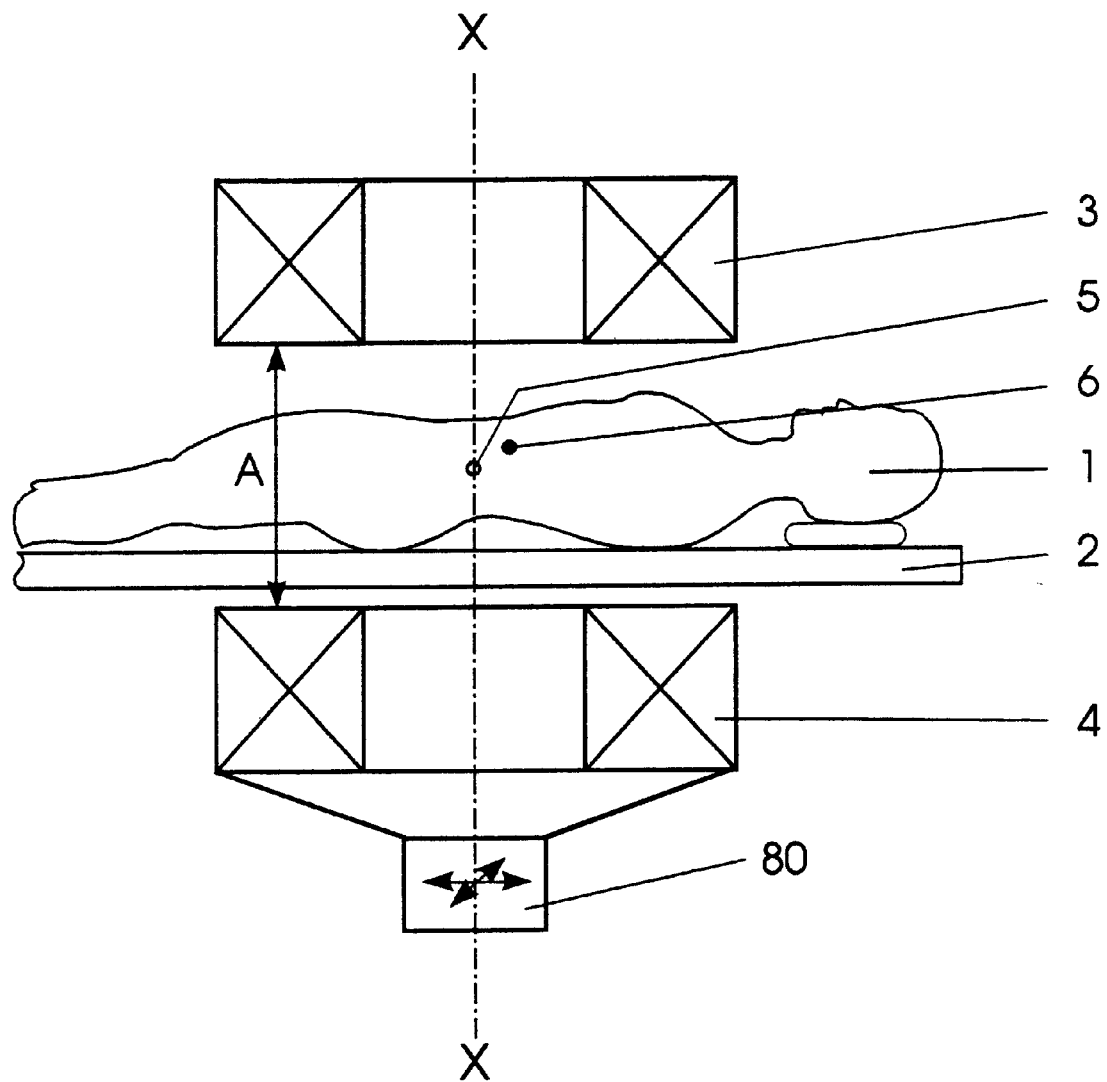
FIG. 1 shows the positioning of a patient in an arrangement according to the invention.
Figure 3:
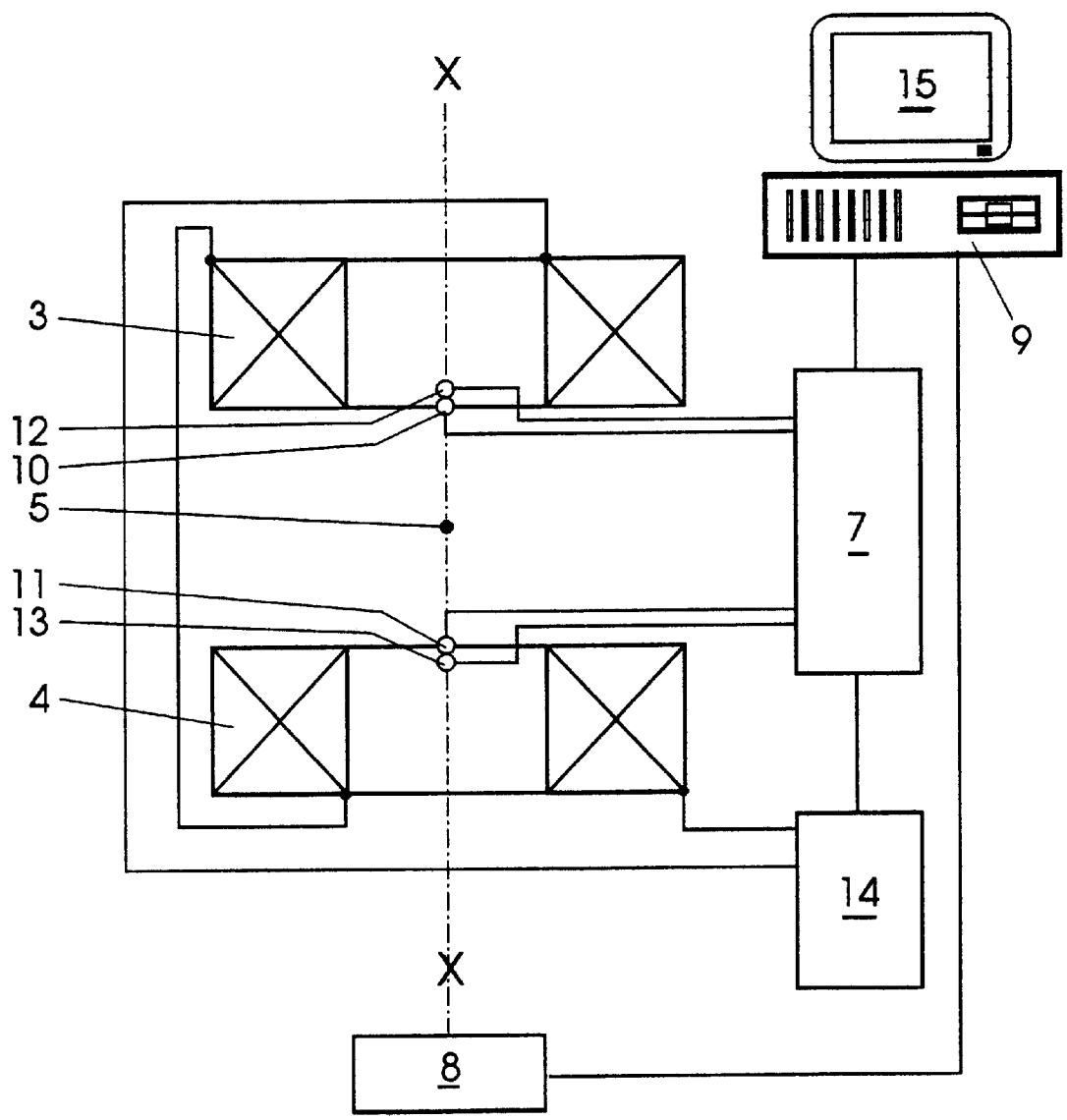
FIG. 3 is an extended representation of an entire arrangement according to the invention, and FIG. 4 a diagram illustrating the coils as pulsed by the current according to the invention.

In FIG. 1 a patient 1 whose gastro-intestinal tract has to be examined lies on a non-metallic table 2. Two identical coils 3 and 4 are arranged about a common axis X—X via their coil axes, spaced apart at an inside width A, of about 30 cm. Current pulses produced by a pulse generator 14, explained in more detail in FIG. 3, are applied across the coils 3, 4. Thus, a maximum primary magnetic field having, for example, a strength of 20000 A/m is produced in a central position 5 at time intervals of 1 s, depending on the current pulse frequency selected. A marker 6, which is made of $\gamma$-$Fe_2O_3$ and has a diameter of about 8 mm, is orally given to the patient 1. After each magnetic charging of the primary magnetic field, the marker 6 has a residual magnetic moment m of about $7 \cdot 10^{-5}$ $Am^2$.

Figure 2:
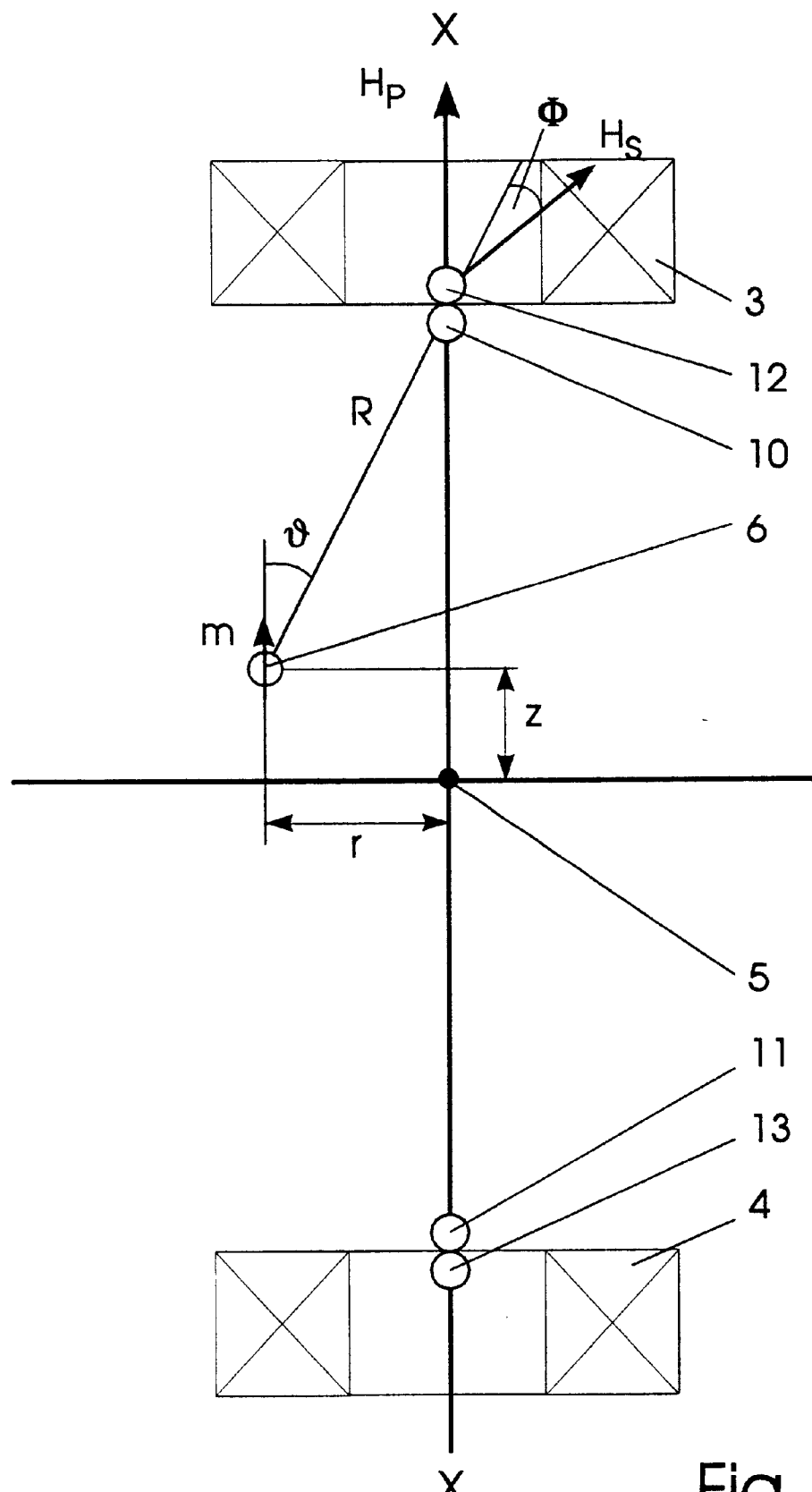
FIG. 2 is a schematical representation of the conditions of deviation of a marker from the coil axis.
Figure 4:
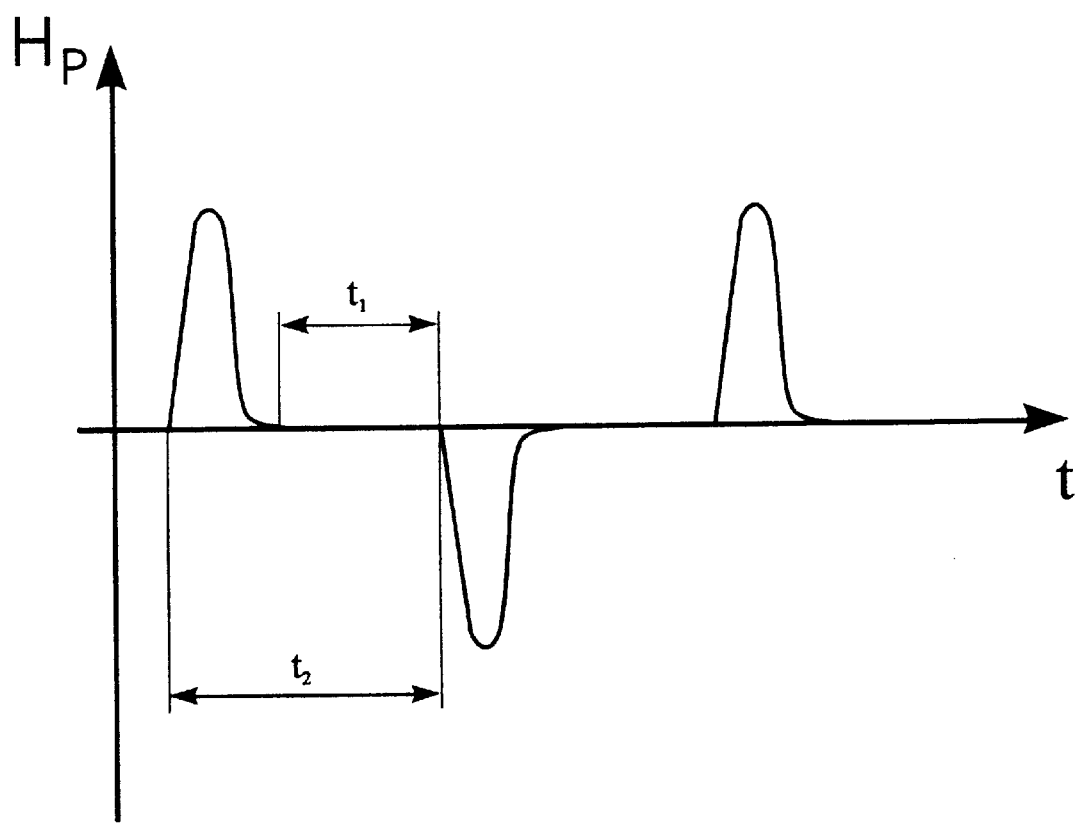

FIG. 2 schematically indicates the rigid connection between the coils 3, 4 and the respective anisotropic magneto-resistive magnetic field sensors 10, 11, 12, 13. The magnetic field sensors 10, 11 are conceived to exclusively detect a component of a secondary magnetic field originating from the marker which is in parallel to the axis X—X, whereas the magnetic field sensors 12, 13 are employed to detect a radial component of the secondary magnetic field which is at right angles to the axis X—X. In accordance with the above measures, the magnetic field component $H_S^{\parallel}$ is about $4 \cdot 10^{-2}$ A/m at the place of the magnetic field sensors 10, 11 when the marker 6 is in the center of the common coil axis X—X, whereas the magnetic field component $H_S^{\perp}$, which is at right angles thereto, is zero. Furthermore, FIG. 2 indicates relations which result from a radial displacement of the marker 6 from the central position 5 relative to the field axis by, for example, r=1 cm. Then, for example, the radial component of the secondary magnetic field is about $4 \cdot 10^{-3}$ A/m at the place of the radial sensors 12, 13. As indicated, the axial component of the secondary magnetic field is about $5.2 \cdot 10^{-2}$ A/m at the place of the sensor 10 when the marker 6 is axially displaced by a distance of z=1 cm, whereas at the place of the sensor 11 it only is $3.5 \cdot 10^{-2}$ A/m. Anisotropic magnetic field sensors are capable of supplying signal voltages of $10^{-4}$ volt with a field strength of 1 A/m. When the sensors are activated and triggered at provided intervals $t_1$ (refer to FIG. 4) between two primary field pulses executed at time intervals $t_2$, then the series connected radial sensors 12, 13 produce a pulse-shaped alternating voltage of an amplitude of 0.4 $\mu$V when the marker 6 is radially displaced by r=1 cm. The amplitude can easily be amplified to 40 $\mu$V by means of a selective frequency amplifier 7. It is feasible to displace the common coil axis X—X of the present example until the signal mentioned vanishes. When this occurs the coil axis X—X again is in the marker center. According to the invention, the displacement is achieved by relative tracking means which, in the simplest form, can be embodied by a cross-slide 80 (refer to FIG. 1) connected to the coils 3 and 4. The relative position is detected by a local sensor 8, indicated in FIG. 3, and fed into a storage and evaluation unit 9.

In accordance with the above described example, the two axial sensors 10, 11 produce a pulse-shaped alternating voltage having amplitudes of about 5.2 $\mu$V (at the sensor 10) and 3.5 $\mu$V (at the sensor 11), respectively, when the marker 6 is axially displaced off from the center 5 by about z=1 cm. It is feasible to amplify the difference of 1.7 $\mu$V to about 170 $\mu$V by means of the selective frequency amplifier 7. The signals indicative of the respective vertical marker position are also fed into the storage and evaluation unit 9. Hence, the required number of measuring values is provided for each actual marker position to uniquely describe the actual local position of the marker in the gastro-intestinal tract. The marker positions, successively obtained in the way described, form a train of points which represent the way of the marker 6. A quotient of the space between adjacent points and a time interval between the points is a measure of local passage speed of the marker 6 to be detected. The entire measuring data obtained can be displayed in three dimensions on a monitor 15 subsequent to a respective evaluation and calibration operation during or after the examination of the marker passage in the patient.

The employment of two coils 3, 4 as disclosed in connection with the above example is a particularly advantageous embodiment, but is not restricting the invention thereto. Embodiments employing only one coil or more than two coils in a suitable arrangement are also feasible.

By virtue of the above method and apparatus the patient is not exposed to any radiation and measurements can be repeated at will. A particular advantage of the invention is the absence of expensive screening measures since the magnetic field of the earth and any other local interference fields, respectively, have no affect on the finding of the measuring result.

We claim:

1. An apparatus for determining a position of a marker in an organic cavity comprising
    said marker being a magnetizable marker formed of a magnetizable material and having a marker diameter;
    at least one electric coil having a coil diameter of at least fivefold said marker diameter and defining a coil axis;
    means for applying successive current pulses through said at least one electric coil;
    anisotropic magnetic field sensors being arranged in axial symmetry to said coil axis and being connected in fixed relation to said at least one electric coil;
    means for moving said at least one electric coil and thereby said coil axis relative to the organic cavity and said marker within said organic cavity and means for detecting a position of the coil axis with relation to the organic cavity;
    means for detecting, storing and evaluating signals from said anisotropic magnetic field sensors; and
    means for detecting the position of said marker based on comparing successive ones of said signals from said anisotropic magnetic field sensors obtained between respective successive ones of said successive current pulses while actuating said means for moving said at least one electric coil in accordance with said comparison.

2. The apparatus according to claim 1, wherein said at least one electric coil is adapted to generate an axially symmetrical and substantially homogeneous primary magnetic field, over a measuring range of about $10 \cdot 10 \cdot 30$ cm$^3$.

3. The apparatus according to claim 1 or 2, wherein said at least one electric coil is two coils arranged coaxially with one another and spaced apart by a coil spacing distance defining a volume in which said organic cavity is inserted between said two coils.

4. The apparatus according to claim 1, wherein the marker is spherosymmetrically embodied and made of an isotropic magnetic material exhibiting a coercive field strength over a range of from $10^4$ up to $10^5$ A/m.

5. The apparatus according to claim 4, wherein the marker substantially is made of at least one of $\gamma$—Fe$_2$O$_3$ and Fe$_3$O$_4$.

6. An apparatus for determining a position of a marker in an organic cavity comprising:
    said marker being a magnetizable marker formed of a magnetizable material and having a marker diameter;
    at least one electric coil having a coil diameter of at least fivefold said marker diameter and defining a coil axis;
    means for applying successive current pulses through said at least one electric coil;
    anisotropic magnetic field sensors being arranged in axial symmetry to said coil axis and being connected in fixed relation to said at least one electric coil;
    means for moving said at least one electric coil and thereby said coil axis relative to the organic cavity and said marker within said organic cavity and means for detecting a position of the coil axis with relation to the organic cavity;
    means for detecting, storing and evaluating signals from said anisotropic magnetic field sensors,
    means for detecting the position of said marker based on comparing successive ones of said signals from said anisotropic magnetic field sensors obtained between respective successive ones of said successive current pulses while actuating said means for moving said at least one electric coil in accordance with said comparison;

at least one of said anisotropic magnetic field sensors being positioned along the coil axis to detect a parallel magnetic field component of a secondary magnetic field of the marker which is parallel to the coil axis; and at least one of said anisotropic magnetic field sensors being positioned to detect a radial magnetic field component of the secondary magnetic field of the marker which is at right angles to the coil axis.

7. The apparatus according to claim 6, characterized in that magneto-resistive thin layer sensors are selected wherein said anisotropic magnetic field sensors are magneto-resistive thin layer sensors.

8. An apparatus for determining a position of a marker in an organic cavity comprising:

said marker being a magnetizable marker formed of a magnetizable material and having a marker diameter;

at least one electric coil having a coil diameter of at least fivefold said marker diameter and defining a coil axis;

means for applying successive current pulses through said at least one electric coil;

anisotropic magnetic field sensors being arranged in axial symmetry to said coil axis and being connected in fixed relation to said at least one electric coil;

means for moving said at least one electric coil and thereby said coil axis relative to the organic cavity and said marker within said organic cavity and means for detecting a position of the coil axis with relation to the organic cavity;

means for detecting storing and evaluating signals from said anisotropic magnetic field sensors;

means for detecting the position of said marker based on comparing successive ones of said signals from said anisotropic magnetic field sensors obtained between respective successive ones of said successive current pulses while actuating said means for moving said at least one electric coil in accordance with said comparison;

said anisotropic magnetic field sensors including a plurality of anisotropic magnetic field sensors for detecting a radial magnetic field component of a secondary magnetic field of the marker which is at right angles to the coil axis, and said plurality of anisotropic magnetic field sensors being arranged in axial symmetry to the coil axis and in a plane at right angles to the coil axis.

9. The apparatus according to claims 1 and 6, wherein said anisotropic magnetic field sensors are arranged in spaced relation to the marker at at least three-times the marker diameter.

10. The apparatus as claimed in claim 4, wherein the isotropic magnetic material has a relative residual magnetism of greater than 0.8.

11. The apparatus as claimed in any one of claims 1, 7 and 8, further comprising control means for controlling said means for applying successive current pulses to apply successive current pulses of alternating polarities at respective time intervals to produce secondary magnetic fields of said marker having alternating polarities and said means for detecting compares said signals to detect said secondary magnetic fields of alternating polarities.

12. A method for determining a position of a marker in an organic cavity comprising the steps of:

providing said marker as a magnetizable marker formed of a magnetizable material and having a marker diameter;

providing at least one electric coil having a coil diameter of at least fivefold said marker diameter and defining a coil axis;

providing means for applying current pulses through said at least one electric coil;

providing anisotropic magnetic field sensors arranged in axial symmetry to said coil axis and connected in fixed relation to said at least one electric coil;

providing means for moving said at least one electric coil and thereby said coil axis relative to the organic cavity and said marker within said organic cavity, and means for detecting a position of the coil axis with relation to the organic cavity;

providing means for detecting, storing and evaluating signals from said anisotropic magnetic field sensors;

disposing said organic cavity with said marker disposed therein proximate said at least one electric coil and generally along the coil axis such that said marker is within a substantially uniform region of a magnetic field produce by said at least one coil;

applying successive current pulses of alternating polarities at respective time intervals across said at least one coil using said means for applying current pulses to magnetize said marker to produce a secondary magnetic field having alternating polarities;

detecting, subsequent to application of respective ones of said current pulses, parallel and perpendicular magnetic field components of said secondary magnetic field originating from said marker, oriented respectively parallel and perpendicular to the coil axis, by use of said anisotropic magnetic field sensors between applications of said current pulses;

displacing said at least one electric coil using said means for moving, relative to the organic cavity containing the marker until detecting a minimal level of said perpendicular magnetic field component; and displaying a position of the coil axis related to the organic cavity and measured values of the parallel magnetic field component of the marker when the minimal level of said perpendicular magnetic field component is detected.

13. The method according to claim 12, wherein signals of the anisotropic magnetic field sensors generated by the secondary magnetic field of the marker are measured at a point of time when a primary magnetic field produced by the at least one electric coil has decayed to less than 10% of a maximum thereof at a time between two of said successive current pulses.

14. The method according to claim 12, or 11, wherein a plurality of measurements of the secondary magnetic field is carried out between two of said successive current pulses applied across the electric coil, and the measuring values are submitted to a mean value formation.

15. The method according to claims 12, or 11, wherein a time interval between two successive ones of said successive current pulses is less than 10 s.

* * * * *